US006949816B2

(12) United States Patent
Brown et al.

(10) Patent No.: US 6,949,816 B2
(45) Date of Patent: Sep. 27, 2005

(54) SEMICONDUCTOR COMPONENT HAVING FIRST SURFACE AREA FOR ELECTRICALLY COUPLING TO A SEMICONDUCTOR CHIP AND SECOND SURFACE AREA FOR ELECTRICALLY COUPLING TO A SUBSTRATE, AND METHOD OF MANUFACTURING SAME

(75) Inventors: Clem H. Brown, Scottsdale, AZ (US); Wai Wong Chow, Sheung Shui (HK); Frank J. Mosna, Jr., Tempe, AZ (US)

(73) Assignee: Motorola, Inc., Schaumburg, IL (US)

( * ) Notice: Subject to any disclaimer, the term of this patent is extended or adjusted under 35 U.S.C. 154(b) by 16 days.

(21) Appl. No.: 10/420,054

(22) Filed: Apr. 21, 2003

(65) Prior Publication Data

US 2004/0207054 A1 Oct. 21, 2004

(51) Int. Cl.[7] .................... H01L 23/495; H01L 23/48
(52) U.S. Cl. .................... 257/684; 257/666; 257/696; 257/698; 257/691; 257/796; 257/730; 257/787; 257/670; 257/784; 257/786; 257/676; 257/675; 257/775; 257/776; 257/734; 174/52.1
(58) Field of Search ................... 257/775, 776, 257/737, 738, 674–676, 696, 698, 690–693, 796, 784, 786, 678, 687, 730, 773, 670, 734; 174/52.1

(56) References Cited

U.S. PATENT DOCUMENTS

| 5,147,815 A | | 9/1992 | Casto | |
|---|---|---|---|---|
| 5,172,214 A | | 12/1992 | Casto | |
| 6,143,981 A | | 11/2000 | Glenn | |
| 6,201,292 B1 | * | 3/2001 | Yagi et al. | 257/666 |
| 6,242,284 B1 | * | 6/2001 | Kang et al. | 438/106 |
| 6,281,568 B1 | | 8/2001 | Glenn et al. | |
| 6,448,107 B1 | * | 9/2002 | Hong et al. | 438/106 |
| 6,452,255 B1 | * | 9/2002 | Bayan et al. | 257/666 |
| 6,498,099 B1 | * | 12/2002 | McLellan et al. | 438/689 |
| 6,562,660 B1 | * | 5/2003 | Sakamoto et al. | 438/124 |
| 6,777,788 B1 | * | 8/2004 | Wan et al. | 257/670 |
| 2003/0015774 A1 | * | 1/2003 | Auburger et al. | 257/666 |
| 2003/0057542 A1 | * | 3/2003 | Frezza et al. | 257/693 |
| 2003/0067058 A1 | * | 4/2003 | Abe et al. | 257/666 |

* cited by examiner

*Primary Examiner*—Alexander Oscar Williams
(74) *Attorney, Agent, or Firm*—Bryan Cave LLP

(57) ABSTRACT

A semiconductor component for electrical coupling to a substrate (230) includes: a semiconductor chip (110); a non-leaded leadframe (120) including a plurality of electrical contacts (130) located around a periphery (111) of the semiconductor chip; a first electrical conductor (140) electrically coupling together the semiconductor chip and the non-leaded leadframe; and a mold compound (210) disposed around the semiconductor chip, the first electrical conductor, and the plurality of electrical contacts. At least one electrical contact of the plurality of electrical contacts includes: a first surface (310) having a first surface area for electrically coupling to the semiconductor chip; and a second surface (320) opposite the first surface and having a second surface area for electrically coupling to the substrate, where the second surface area is larger than the first surface area.

27 Claims, 3 Drawing Sheets

US 6,949,816 B2

SEMICONDUCTOR COMPONENT HAVING FIRST SURFACE AREA FOR ELECTRICALLY COUPLING TO A SEMICONDUCTOR CHIP AND SECOND SURFACE AREA FOR ELECTRICALLY COUPLING TO A SUBSTRATE, AND METHOD OF MANUFACTURING SAME

FIELD OF THE INVENTION

This invention relates generally to semiconductor components, and relates more particularly to leadframes for semiconductor components.

BACKGROUND OF THE INVENTION

Surface mount packages containing semiconductor chips and other electronic devices include electrical contacts for electrical coupling to a substrate, such as a printed circuit board. Frequently, a quantity of solder is placed on one or more of the electrical contacts to form solder joints that accomplish the electrical coupling. For surface mount packages utilizing solder joints in this way, solder joint reliability is an important design issue. Larger solder joints tend to be more robust and to last longer than smaller solder joints; so for solder joint reliability, larger solder joints are preferred. However, larger solder joints require larger electrical contacts on which to place the solder joints, and larger electrical contacts lead to larger packages that are less cost-effective and less competitive.

The size of the electrical contacts, as well as their pitch, is dictated by the thickness of the leadframe and by the etch process used to produce the desired pattern in the leadframe. Thicker leadframes require larger electrical contacts. Surface mount packages, such as a power quad flat non-leaded (QFN) package, designed for high power applications must be relatively thick in order to support the thermal requirements of the high power application. In conventional leadframe technology, these thick leadframes lead to low solder joint reliability, large, inefficient package sizes, or both. Accordingly, a need exists for a cost-effective, efficient leadframe having electrical contacts that are closely spaced and that offer good solder joint reliability.

BRIEF DESCRIPTION OF THE DRAWINGS

The invention will be better understood from a reading of the following detailed description, taken in conjunction with the accompanying figures in the drawings in which.

Figure 1:
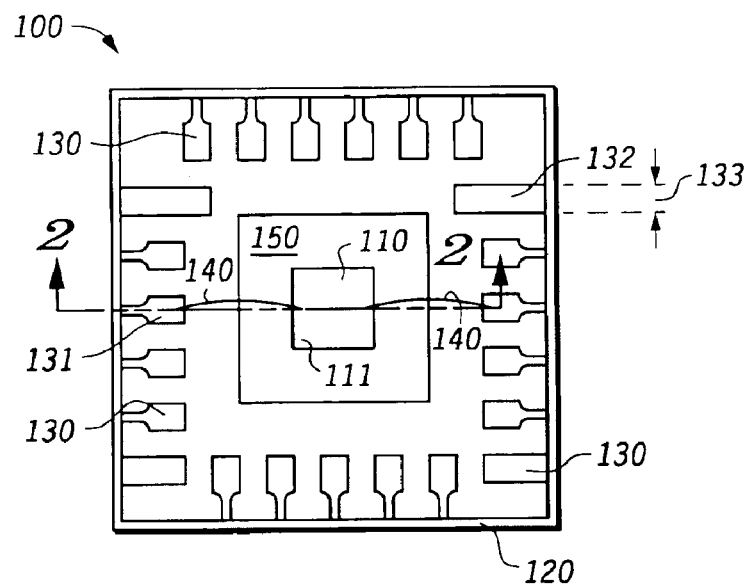
FIG. 1 is a top view of a semiconductor component after a first portion of a method of manufacturing the semiconductor component and according to an embodiment of the invention.

For simplicity and clarity of illustration, the drawing figures illustrate the general manner of construction, and descriptions and details of well-known features and techniques may be omitted to avoid unnecessarily obscuring the invention. Additionally, elements in the drawing figures are not necessarily drawn to scale. For example, the dimensions of some of the elements in the figures may be exaggerated relative to other elements to help improve understanding of embodiments of the present invention. The same reference numerals in different figures denote the same elements.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments of the invention described herein are, for example, capable of operation in sequences other than those illustrated or otherwise described herein. Furthermore, the terms "comprise," "include," "have," and any variations thereof, are intended to cover a non-exclusive inclusion, such that a process, method, article, or apparatus that comprises a list of elements is not necessarily limited to those elements, but may include other elements not expressly listed or inherent to such process, method, article, or apparatus.

The terms "left," "right," "front," "back," "top," "bottom," "over," "under, " and the like in the description and in the claims, if any, are used for descriptive purposes and not necessarily for describing permanent relative positions. It is to be understood that the terms so used are interchangeable under appropriate circumstances such that the embodiments of the invention described herein are, for example, capable of operation in other orientations than those illustrated or otherwise described herein. The term "coupled," as used herein, is defined as directly or indirectly connected in an electrical or non-electrical manner.

DETAILED DESCRIPTION OF THE DRAWINGS

FIG. 1 is a top view of a semiconductor component 100 for electrical coupling to a substrate (not shown in FIG. 1) according to an embodiment of the invention. Semiconductor component 100 comprises a semiconductor chip 110, a non-leaded leadframe 120 comprising a plurality of electrical contacts 130 located around a periphery 111 of semiconductor chip 110, and electrical conductors 140 electrically coupling together semiconductor chip 110 and non-leaded leadframe 120. As an example, electrical conductors 140 can comprise one or more of the following electrical conductors: wire bonds, solder, electrically conductive adhesive, a TAB bonding structure, or the like, and plurality of electrical contacts 130 comprises one or more of an electrical contact 131. Additional details regarding electrical contact 131 are explained hereinafter. Semiconductor component 100 can further comprise an optional chip mounting structure or flag 150, over which semiconductor chip 110 can be mounted. Flag 150 can be part of or separate from non-leaded leadframe 120.

Figure 2:
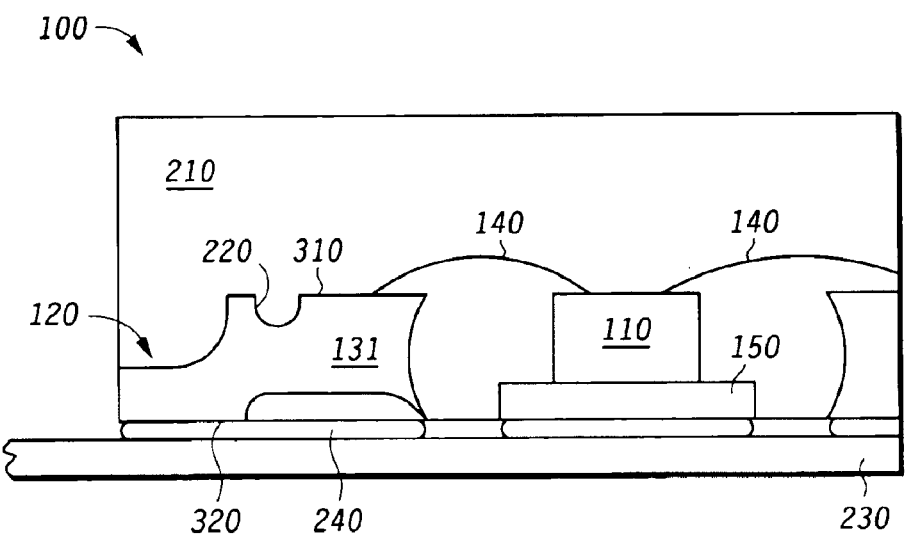
FIG. 2 is a cross-sectional view of the semiconductor component of FIG. 1 after a subsequent portion of the method of manufacturing the semiconductor component and taken along a section line 2—2 in FIG. 1.

FIG. 2 is a cross-sectional view of semiconductor component 100 of FIG. 1 after subsequent processing steps and taken along a section line 2—2 in FIG. 1. FIG. 2 illustrates semiconductor component 100 to further comprise a mold compound 210 disposed around semiconductor chip 110, electrical conductor 140, flag 150, and plurality of electrical contacts 130, including electrical contacts 131. Electrical contact 131 is electrically coupled to a substrate 230. Other electrical contacts of plurality of electrical contacts 130 (FIG. 1) can also be electrically coupled to substrate 230, and flag 150 can be electrically and/or thermally coupled to substrate 230. In one embodiment, substrate 230 can be an electronic substrate, such as a printed circuit board, another electronic component, or the like. Additional details regarding electrical contact 131 are explained hereinafter.

Figure 3:
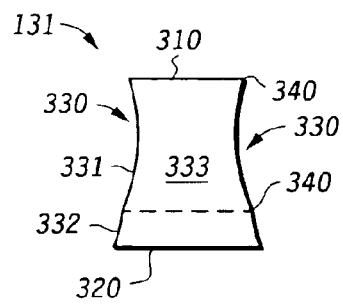
FIG. 3 is a front elevational view of an electrical contact according to an embodiment of the invention.

FIG. 3 is a front elevational view of electrical contact 131 of plurality of electrical contacts 130 according to an embodiment of the invention. Electrical contact 131 comprises a surface 310 having a first surface area for electrically coupling electrical conductor 140 between electrical contact 131 and semiconductor chip 110 (as shown in FIG. 1), and a surface 320 opposite surface 310 and having a second surface area for electrically coupling to substrate 230 (as shown in FIG. 2). Electrical contact 131 further comprises opposite, but symmetric, side surfaces 330 and a front surface 333 coupling together surfaces 310 and 320. Side surface 330 has a concave section 331 and a concave section 332 adjacent to concave section 331. Concave section 331 is located between surface 310 and concave section 332, and concave section 332 is located between surface 320 and concave section 331. In one embodiment, concave section 331 has a first radius of curvature, and concave section 332 has a second radius of curvature less than the first radius of curvature. In the same or another embodiment, concave sections 331 and 332 form at least one mold lock feature 340. As an example, mold lock feature 340 can be a vertical mold lock feature, where "vertical" means substantially perpendicular to surface 320. Mold lock feature 340 can be a vertical mold lock feature in the sense that it can inhibit the vertical motion of mold compound 210 (FIG. 2) such that mold compound 210 stays in place after being disposed and cured around non-leaded leadframe 120 (FIGS. 1 and 2). In another embodiment, concave section 331 and/or concave section 332 are themselves vertical mold lock features.

The electrical coupling of surface 320 to substrate 230 (FIG. 2) can be accomplished via an electrical conductor 240 (FIG. 2) such as solder, electrically conductive adhesive, or the like. The second surface area of surface 320 of electrical contact 131 is larger than the first surface area of surface 310 of electrical contact 131. As best seen in FIG. 3, electrical contact 131 has a roughly trapezoidal cross-sectional shape, which provides at least the following advantages and/or benefits: the relatively larger surface 320 provides sufficient area for a relatively large, robust, and reliable solder joint to be placed thereon, while the relatively smaller surface 310 allows non-leaded leadframe 120 to maintain an internal pitch commensurate with the leadframe-thickness-driven aspect ratio.

As illustrated in FIG. 2, surface 310 comprises at least one mold lock feature 220. As an example, mold lock feature 220 can comprise a notch or recess within surface 310. As a further example, mold lock feature 220 can be a horizontal mold lock feature, where "horizontal" means substantially parallel to surface 310. Mold lock feature 220 can be a horizontal mold lock feature in the sense that it can inhibit the horizontal motion of mold compound 210 such that mold compound 210 stays in place once disposed around non-leaded leadframe 120. It should be understood that the surface area of surface 310 does not include the area within mold lock feature 220.

Figure 4:
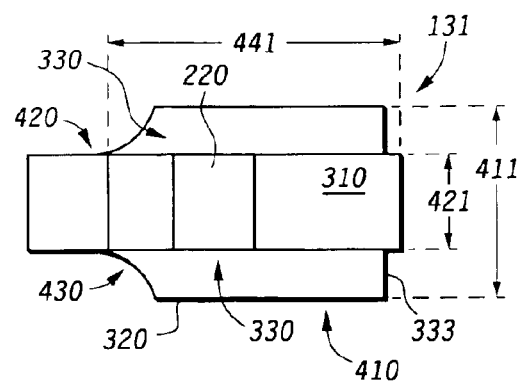
FIG. 4 is a top view of the electrical contact of FIG. 3.
Figure 5:
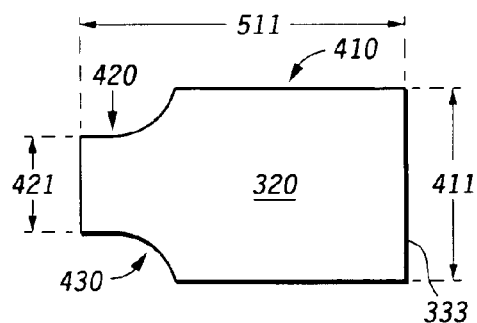
FIG. 5 is a bottom view of the electrical contact of FIG. 3.
Figure 6:
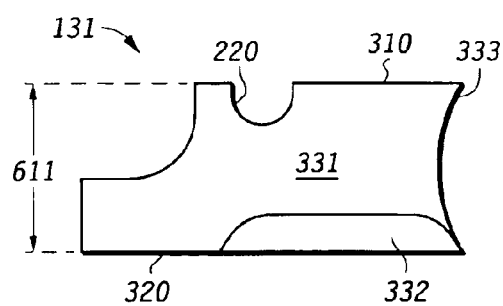
FIG. 6 is a side elevational view of the electrical contact of FIG. 3.

FIGS. 4, 5, and 6 are a top view, a bottom view, and a side elevational view, respectively, of electrical contact 131. As illustrated in FIG. 5, surface 320 of electrical contact 131 comprises a section 410 having a width 411 and a section 420 having a width 421 less than width 411. Surface 320 has a length 511. Surface 320 further comprises a section 430 coupling together sections 410 and 420. As illustrated in FIG. 4, surface 310 has a length 441 and width 421. For high power applications, non-leaded leadframe 120 may advantageously have a thickness 611 (FIG. 6) of at least approximately 0.5 centimeters (cm). In the same or another embodiment, width 411 may be approximately 0.5 to 0.6 millimeters (mm); width 421 may be approximately 0.2 to 0.4 mm; length 441 may be approximately 0.7 to 0.9 mm; and length 511 may be approximately 0.7 to 0.8 mm. In one embodiment, surface 310 and surface 320 can have lengths substantially similar to each other.

Semiconductor component 100 may further comprise an electrical contact 132 (FIG. 1) of plurality of electrical contacts 130. Electrical contact 132 comprises a bottom surface similar to surface 320 (FIG. 2) and having a substantially constant width 133. In one embodiment, width 133 may be substantially equal to width 411 (FIGS. 4 and 5). In the same or another embodiment, the bottom surface of electrical contact 132 can be rectangular or square.

Figure 7:
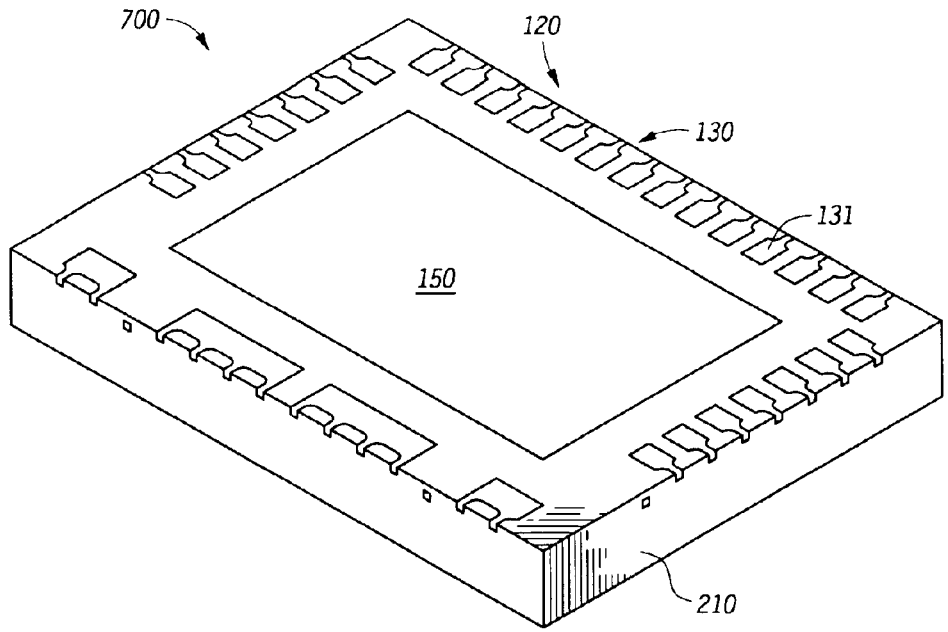
FIG. 7 is a bottom isometric view of a semiconductor component according to an embodiment of the invention.

FIG. 7 is a bottom isometric view of a semiconductor component 700 according to an embodiment of the invention. FIG. 7 depicts non-leaded leadframe 120 after mold compound 210 has been disposed around flag 150, semiconductor chip 110 (FIG. 1), electrical conductors 140 (FIG. 1), and electrical contacts 130, including electrical contact 131, and also after the dam and tie bars are removed from non-leaded leadframe 120.

Figure 8:
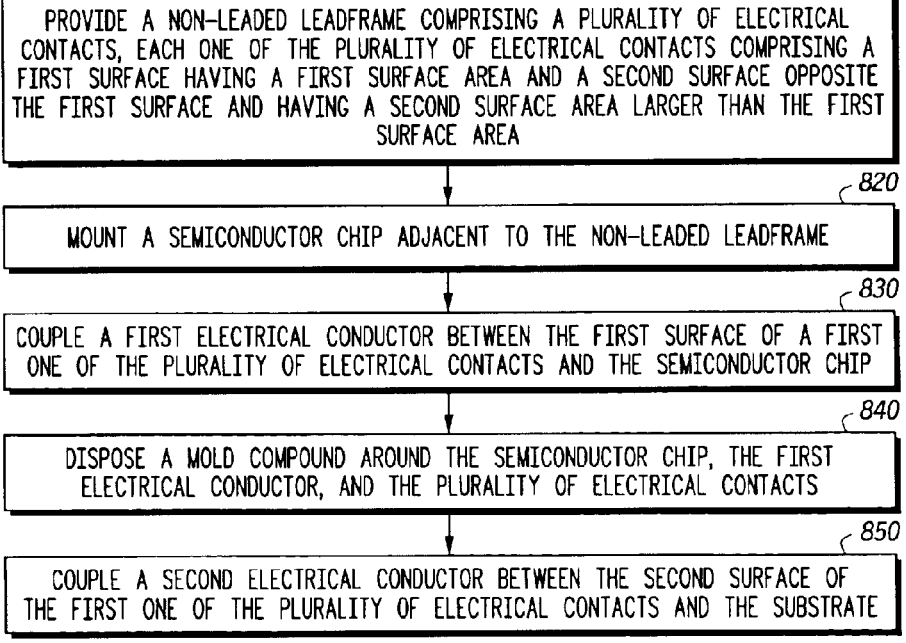
FIG. 8 is a flow chart illustrating a method of manufacturing a semiconductor component according to an embodiment of the invention.

FIG. 8 is a flow chart illustrating a method 800 of manufacturing a semiconductor component for electrical coupling to a substrate according to an embodiment of the invention. A step 810 of method 800 is to provide a non-leaded leadframe comprising a plurality of electrical contacts, each one of the plurality of electrical contacts comprising a first surface having a first surface area and a second surface opposite the first surface and having a second surface area larger than the first surface area. As an example, the non-leaded leadframe can be similar to non-leaded leadframe 120 in FIGS. 1 and 7.

A step 820 of method 800 is to mount a semiconductor chip adjacent to and/or over the non-leaded leadframe. As an example, the semiconductor chip can be similar to semiconductor chip 110 in FIGS. 1 and 2. A step 830 of method 800 is to electrically couple a first electrical conductor between the first surface of a first one of the plurality of electrical contacts and the semiconductor chip. As an example, the first electrical conductor can be similar to electrical conductors 140 in FIGS. 1 and 2.

A step 840 of method 800 is to dispose a mold compound around the semiconductor chip, the first electrical conductor, and the plurality of electrical contacts. As an example, the mold compound can be similar to mold compound 210 in FIGS. 2 and 7. A step 850 of method 800 is to electrically couple a second electrical conductor between the second surface of the first one of the plurality of electrical contacts and the substrate. As an example, the second electrical conductor can be similar to electrical conductor 240 in FIG. 2, and the substrate can be similar to substrate 230 in FIG. 2.

Although the invention has been described with reference to specific embodiments, it will be understood by those skilled in the art that various changes may be made without departing from the spirit or scope of the invention. Various examples of such changes have been given in the foregoing description. Accordingly, the disclosure of embodiments of the invention is intended to be illustrative of the scope of the invention and is not intended to be limiting. It is intended that the scope of the invention shall be limited only to the extent required by the appended claims. For example, to one of ordinary skill in the art, it will be readily apparent that the semiconductor component for electrical coupling to a substrate discussed herein may be implemented in a variety of embodiments, and that the foregoing discussion of certain of these embodiments does not necessarily represent a complete description of all possible embodiments.

Additionally, benefits, other advantages, and solutions to problems have been described with regard to specific embodiments. The benefits, advantages, solutions to problems, and any element or elements that may cause any benefit, advantage, or solution to occur or become more pronounced, however, are not to be construed as critical, required, or essential features or elements of any or all of the claims.

Moreover, embodiments and limitations disclosed herein are not dedicated to the public under the doctrine of dedication if the embodiments and/or limitations: (1) are not expressly claimed in the claims; and (2) are or are potentially equivalents of express elements and/or limitations in the claims under the doctrine of equivalents.

What is claimed is:

1. A semiconductor component for electrical coupling to a substrate, the semiconductor component comprising:
   a semiconductor chip;
   a non-leaded leadframe comprising a plurality of electrical contacts located around a periphery of the semiconductor chip;
   a first electrical conductor electrically coupling together the semiconductor chip and the non-leaded leadframe; and
   a mold compound disposed around the semiconductor chip, the first electrical conductor, and the plurality of electrical contacts,
   wherein:
      at least one electrical contact of the plurality of electrical contacts comprises:
         a first surface having a first surface area for electrically coupling to the semiconductor chip;
         a second surface opposite the first surface and having a second surface area for electrically coupling to the substrate; and
         a side surface coupling together the first surface and the second surface;
      the side surface has a first concave section and a second concave section adjacent to the first concave section; and
      the second surface area is larger than the first surface area.

2. The semiconductor component of claim 1 wherein:
the at least one electrical contact comprises a trapezoidal cross-sectional shape.

3. The semiconductor component of claim 1 wherein:
the first concave section and the second concave section form at least one mold lock feature.

4. The semiconductor component of claim 1 wherein:
the first concave section is located between the first surface and the second concave section; and
the second concave section is located between the second surface and the first concave section.

5. The semiconductor component of claim 1 wherein:
the first concave section has a first radius of curvature; and
the second concave section has a second radius of curvature less than the first radius of curvature.

6. The semiconductor component of claim 1 wherein:
the at least one electrical contact further comprises:
a side surface coupling the first surface to the second surface and comprising at least one mold lock feature.

7. The semiconductor component of claim 1 wherein:
the first surface comprises at least one mold lock feature.

8. The semiconductor component of claim 7 wherein:
the at least one mold lock feature comprises a recess within the first surface.

9. The semiconductor component of claim 1 wherein:
the second surface has a substantially constant width.

10. The semiconductor component of claim 1 wherein:
the second surface has a first section having a first width and a second section having a second width; and
the second width is less than the first width.

11. The semiconductor component of claim 1 wherein:
the first surface has a first length and a first width;
the second surface has the first length and a second width; and
the second width is greater than the first width.

12. The semiconductor component of claim 1 wherein:
the non-leaded leadframe has a thickness of at least 0.5 centimeters.

13. The semiconductor component of claim 1 wherein:
the second surface of the at least one electrical contact has a first section having a first width and a second section having a second width;
the second width is less than the first width; and
the second surface of another electrical contact of the plurality of electrical contacts has a substantially constant width substantially equal to the first width.

14. A semiconductor component for electrical coupling to a substrate, the semiconductor component comprising:
   a semiconductor chip;
   a non-leaded leadframe comprising a plurality of electrical contacts located around a periphery of the semiconductor chip; and
   a mold compound disposed around the semiconductor chip and the plurality of electrical contacts;
   wherein:
      each electrical contact in the plurality of electrical contacts comprises:
         a first surface having a first surface area for electrical coupling to the semiconductor chip;
         a second surface opposite the first surface and having a second surface area for electrical coupling to the substrate; and
         a side surface coupling together the first surface and the second surface;
      the second surface area is larger than the first surface area;
      each electrical contact of the plurality of electrical contacts comprises a trapezoidal cross-sectional shape;
      each side surface comprises at least one mold lock feature; and
      the at least one mold lock feature comprises:
         a first mold lock feature comprising a first concave section in the side surface; and a second mold lock feature comprising a second concave section in the side surface and adjacent to the first concave section.

15. The semiconductor component of claim 14 wherein:
the first concave section has a first radius of curvature; and
the second concave section has a second radius of curvature less than the first radius of curvature.

16. The semiconductor component of claim 14 wherein:
the first mold lock feature is located between the first surface and the second mold lock feature; and
the second mold lock feature is located between the second surface and the first mold lock feature.

17. The semiconductor component of claim 14 wherein:
the first surface comprises a first mold lock feature.

18. The semiconductor component of claim 17 wherein:
the first mold lock feature comprises a notch.

19. The semiconductor component of claim 17 wherein:
the first mold lock feature comprises a notch; and
the at least one mold lock feature comprises:
    a second mold lock feature comprising a first concave section in the side surface; and
    a third mold lock feature comprising a second concave section in the side surface and adjacent to the second mold lock feature.

20. The semiconductor component of claim 19 wherein:
the second mold lock feature is located between the first surface and the third mold lock feature; and
the third mold lock feature is located between the second surface and the second mold lock feature.

21. The semiconductor component of claim 17 wherein:
the second surface has a substantially constant width.

22. The semiconductor component of claim 17 wherein:
the second surface has a first section having a first width, a second section having a second width, and a third section coupling together the first section and the second section; and
the second width is less than the first width.

23. The semiconductor component of claim 22 wherein:
the first surface has a first length and the second width; and
the second surface has the first length.

24. The semiconductor component of claim 22 wherein:
the first surface has a first length and the second width; and
the second surface has a second length greater than the first length.

25. The semiconductor component of claim 24 wherein:
the second surface of a second one of the plurality of electrical contacts has a constant width substantially equal to the first width.

26. The semiconductor component of claim 14 wherein:
the non-leaded leadframe has a thickness of at least 0.5 centimeters.

27. A method of manufacturing a semiconductor component for electrical coupling to a substrate, the method comprising:
providing a non-leaded leadframe comprising:
    a plurality of electrical contacts;
    wherein:
        each one of the plurality of electrical contacts comprises:
            a first surface having a first surface area;
            a second surface opposite the first surface and having a second surface area; and
            a side surface coupling together the first surface and the second surface;
        the side surface has a first concave section and a second concave section adjacent to the first concave section; and
        the second surface area is larger than the first surface area;
mounting a semiconductor chip adjacent to the non-leaded leadframe;
coupling a first electrical conductor between the first surface of a first one of the plurality of electrical contacts and the semiconductor chip;
disposing a mold compound around the semiconductor chip, the first electrical conductor, and the plurality of electrical contacts; and
coupling a second electrical conductor between the second surface of the first one of the plurality of electrical contacts and the substrate.

* * * * *

UNITED STATES PATENT AND TRADEMARK OFFICE
CERTIFICATE OF CORRECTION

PATENT NO. : 6,949,816 B2
APPLICATION NO. : 10/420054
DATED : September 27, 2005
INVENTOR(S) : Brown et al.

It is certified that error appears in the above-identified patent and that said Letters Patent is hereby corrected as shown below:

Column 6, line 1, cancel the text beginning with "5. The semiconductor component" to and ending "of curvature." in column 6, line 4, and insert the following claim:

--5. The semiconductor component of claim 4 wherein: the first concave section has a first radius of curvature; and the second concave section has a second radius of curvature less than the first radius of curvature.--

Signed and Sealed this

Sixteenth Day of October, 2007

JON W. DUDAS
*Director of the United States Patent and Trademark Office*